United States Patent [19]

Metcalf et al.

[11] 4,267,374

[45] May 12, 1981

[54] DERIVATIVES OF AMINES AND AMINO ACIDS

[75] Inventors: Brian W. Metcalf, Strasbourg; Michel Jung, Illkirch Graffenstaden; Charles Danzin, Strasbourg, all of France

[73] Assignee: Merrell Toraude et Compagnie, Strasbourg, France

[21] Appl. No.: 52,035

[22] Filed: Jun. 25, 1979

Related U.S. Application Data

[63] Continuation of Ser. No. 812,115, Jul. 1, 1977, abandoned.

[51] Int. Cl.³ .............. C07C 87/24; C07C 103/28; C07C 103/44; C07C 125/06
[52] U.S. Cl. .............................. 564/509; 560/159; 564/159; 564/164; 564/165; 564/197; 564/215; 564/240; 424/300; 424/320; 424/324; 424/325; 424/326
[58] Field of Search .......... 260/583 H, 561 R, 561 A, 260/561 N, 558 A, 559 R, 564 A; 562/553, 561, 562, 563; 560/159

[56] References Cited

U.S. PATENT DOCUMENTS

| | | | |
|---|---|---|---|
| 2,662,915 | 12/1953 | Lontz et al. ...................... | 562/574 |
| 2,766,285 | 10/1956 | Hennion ........................... | 260/583 H |
| 3,959,356 | 5/1976 | Metcalf et al. ................... | 260/293.86 |
| 4,026,925 | 5/1977 | Pigerol et al. ................... | 260/583 H |

OTHER PUBLICATIONS

Relyea, Noel et al., "Potent Inhibition of Ornithine Decarboxylase by Beta, Gamma-Unsaturated Substrate Analogs." Biochem. Biophysics Res. Commun. (1975) 67(1) pp. 392-402.
Rando, Robert R., "Chemistry and Enzymology of $k_{cat}$ Inhibitors." Science, Bol. 185, pp. 320-324, (Jul. 1974).

*Primary Examiner*—Natalie Trousof
*Assistant Examiner*—L. Hendriksen
*Attorney, Agent, or Firm*—John J. Kolano; Raymond A. McDonald; Salvatore R. Conte

[57] ABSTRACT

Novel compounds of the formula

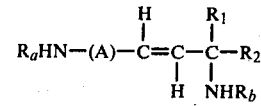

wherein A is methylene, ethylene or ethylidene; $R_1$ is —C≡CH or —CH=CH$_2$; $R_2$ is hydrogen or COR wherein R is hydroxy, a straight or branched alkoxy group of from 1 to 8 carbon atoms, —NR$_4$R$_5$ wherein each of R$_4$ and R$_5$ is hydrogen or a straight or branched lower alkyl group of from 1 to 4 carbon atoms or

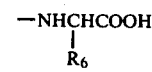

wherein R$_6$ is hydrogen, a straight or branched lower alkyl group of from 1 to 4 carbon atoms, benzyl or p-hydroxybenzyl; R$_a$ is hydrogen,

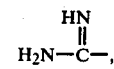

alkylcarbonyl wherein the alkyl moiety has from 1 to 4 carbon atoms and is straight or branched, alkoxycarbonyl wherein the alkoxy moiety has from 1 to 4 carbon atoms and is straight or branched or

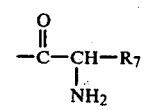

wherein R$_7$ is selected from hydrogen, a straight or branched lower alkyl group of from 1 to 4 carbon atoms, benzyl and p-hydroxybenzyl; and R$_b$ has the same meaning as defined for R$_a$ except R$_b$ is not

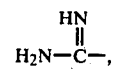

and R$_a$ and R$_b$ can be the same or different; with the provisos that when R$_2$ is hydrogen, R$_1$ is —C≡H; when A is ethylidene, R$_2$ is hydrogen; and when R$_a$ is

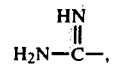

A is methylene; and pharmaceutically acceptable salts and individual optical isomers thereof.

4 Claims, No Drawings

DERIVATIVES OF AMINES AND AMINO ACIDS

This is a continuation of application Ser. No. 812,115, filed July 1, 1977, now abandoned.

FIELD OF INVENTION

This invention relates to novel pharmaceutically useful acetylenic derivatives of amines and amino acids and novel vinyl derivatives of amino acids.

SUMMARY OF INVENTION

The compounds of the present invention are represented by the following general Formula I

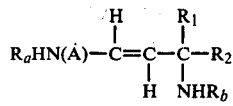
Formula I wherein A is methylene, ethylene or ethylidene; $R_1$ is —C≡CH or —CH=$CH_2$; $R_2$ is hydrogen or COR wherein R is hydroxy, a straight or branched alkoxy group of from 1 to 8 carbon atoms, —$NR_4R_5$ wherein each of $R_4$ and $R_5$ is hydrogen, or a straight or branched lower alkyl group of from 1 to 4 carbon atoms or

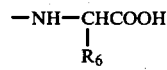

wherein $R_6$ is hydrogen, a straight or branched lower alkyl group of from 1 to 4 carbon atoms, benzyl or p-hydroxybenzyl; $R_a$ is hydrogen,

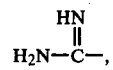

alkylcarbonyl wherein the alkyl moiety has from 1 to 4 carbon atoms and is straight or branched, alkoxycarbonyl wherein the alkoxy moiety has from 1 to 4 carbon atoms and is straight or branched or

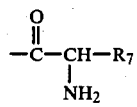

wherein $R_7$ is hydrogen, a straight or branched lower alkyl group of from 1 to 4 carbon atoms, benzyl or p-hydroxybenzyl; and $R_b$ has the same meaning defined for $R_a$ except $R_b$ is not

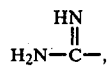

and $R_a$ and $R_b$ can be the same or different; with the provisos that when $R_2$ is hydrogen, $R_1$ is —C≡CH; when A is ethylidene, $R_2$ is hydrogen; and when $R_1$ is

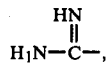

A is methylene.

The pharmaceutically acceptable salts and individual optical isomers of the compounds of general Formula I are included within the scope of the present invention.

DETAILED DESCRIPTION OF INVENTION

In the above general Formula I methylene is taken to mean —$CH_2$—; ethylene is taken to mean —$CH_2CH_2$—; and ethylidene is taken to mean

It is evident from the foregoing general Formula I that the compounds of the present invention are acetylene derivatives of amines and amino acids or are vinyl derivatives of amino acids.

As set forth hereinabove $R_b$ has the same meaning as $R_a$ except $R_b$ is not

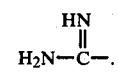

That is, $R_b$ is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

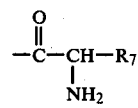

wherein $R_7$ is hydrogen, a straight or branched lower alkyl group of from 1 to 4 carbon atoms, benzyl or p-hydroxybenzyl.

As used in general Formula I the term alkylcarbonyl is taken to mean the group

wherein the alkyl moiety has from 1 to 4 carbon atoms and is straight or branched, for example, methyl, ethyl, n-propyl, isopropyl, n-butyl, isobutyl and tert-butyl.

As used in general Formula I the term alkoxycarbonyl is taken to mean the group

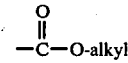

wherein the alkoxy moiety, that is, —O-alkyl, has from 1 to 4 carbon atoms and is straight or branched, for example, methoxy, ethoxy, n-propoxy, isopropoxy, n-butoxy, and tert-butoxy.

Illustrative examples of straight or branched alkyl groups having from 1 to 4 carbon atoms as used in general Formula I are methyl, ethyl, n-propyl, n-butyl, isopropyl and tert-butyl.

Illustrative examples of alkoxy groups having from 1 to 8 carbon atoms as used in general Formula I are methoxy, ethoxy, propoxy, butoxy, pentyloxy, and octyloxy.

Illustrative examples of pharmaceutically acceptable salts of the compounds of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminum, organic amines, such as, primary, secondary or tertiary amines, for example, cyclohexylamine, ethylamine, pyridine, methylamino-ethanol, ethanolamine and piperazine. The salts are prepared by conventional means.

Preferred compounds of this invention are those of general Formula I wherein each of $R_a$ and $R_b$ is hydrogen or alkylcarbonyl wherein the alkyl moiety has from 1 to 4 carbon atoms and is straight or branched with compounds wherein each of $R_a$ and $R_b$ is hydrogen being more preferred. Compounds wherein A is methylene or ethylidene are also preferred with compounds wherein A is methylene being more preferred. Also compounds wherein $R_2$ is hydrogen or COR wherein R is hydroxy or a straight or branched alkoxy group of from 1 to 8 carbon atoms represents another preferred embodiment of this invention.

Illustrative examples of compounds of the present invention are the following:
1,4-hex-2-en-5-ynediamine,
1,5-hept-3-en-6-ynediamine,
2,5-hept-3-en-6-ynediamine,
2-acetylene-2,5-diaminopent-3-enoic acid,
2-acetylene-2,6-diaminohex-3-enoic acid,
2,6-diamino-2-vinylhex-3-enoic acid,
N-(1-acetylene-4-aminobut-2-enyl)-2-aminoacetamide,
N-(1-acetylene-4-aminobut-2-enyl)acetamide,
N-(1-acetylene-5-aminopent-2-enyl)butyramide,
N-(1-acetylene-4-aminopent-2-enyl)acetamide,
methyl N-(1-acetylene-4-aminobut-2-enyl)carbamate,
methyl 2-acetylene-2,6-diaminohex-3-enoate,
tert-butyl 2,5-diamino-2-vinylpent-3-enoate,
n-hexyl 2,6-diamino-2-vinylhex-3-enoate,
ethyl 2-acetylene-5-amino-2-(1-oxoethylamino)pent-3-enoate,
n-butyl 5-amino-2-ethoxycarbonylamino-2-vinylhex-3-enoate,
2-acetylene-5-amino-2-(1-oxoethylamino)hex-3-enamide,
N-ethyl-2-acetylene-2,5-diaminopent-3-enamide,
N,N'-di-n-propyl-5-amino-2-methoxycarbonylamino-2-vinylpent-3-enamide,
2-acetylene-2,5-di-(1-oxopropylamino)pent-3-enoic acid,
isopropyl 2,5-di-(n-butoxycarbonylamino)-2-vinylhex-3-enoate,
2-[2-acetylene-2,5-diamino-1-oxopent-3-enylamino]acetic acid, and
2,5-diamino-2-vinylpent-3-enoic acid.

The compounds of general Formula I are irreversible inhibitors of decarboxylase enzymes which are involved in polyamine formation rendering said compounds useful as pharmacological agents. Polyamines, particularly putrescine, spermidine and spermine are present in plant and animal tissues and in some microorganisms. Although the exact physiological role of polyamines has not been clearly delineated there is evidence to suggest that polyamines are involved with cell division and growth. (H. G. Williams-Ashman et al., The Italian J. Biochem. 25, 5–32 (1976), A. Raina and J. Janne, Med. Biol. 53, 121–147 (1975) and D. H. Russell, Life Sciences 13, 1635–1647 (1973)). Polyamines are essential growth factors for or involved in the growth processes of certain microorganisms, for example, *E. coli*, Enterobacter, Klebsiella, *Staphylococcus aureus, C. cadaveris, Salmonella typhosa* and *Haemophilus parainfluenza*. Polyamines are associated with both normal and neoplastic rapid growth there being an increase in the synthesis and accumulation of polyamines following a stimulus causing cellular proliferation. Also, levels of polyamines are known to be high in embryonic systems, leukemic cells and other rapidly growing tissues. It is known that there is a correlation between the activity of the decarboxylase enzymes of ornithine, S-adenosylmethionine, arginine and lysine and polyamine formation.

The biosyntheses of putrescine, spermidine and spermine are interrelated. Putrescine is the decarboxylation product of ornithine, catalyzed by ornithine decarboxylase. Putrescine formation may also occur by decarboxylation of arginine to form agmatine which is hydrolyzed to give putrescine and urea. Arginine is also involved in ornithine formation by action of the enzyme arginase. Activation of methionine by S-adenosylmethionine synthetase forms S-adenosylmethionine which is decarboxylated, after which the propylamine moiety of activated methionine may be transferred to putrescine to form spermidine and to spermidine to form spermine. Hence, putrescine serves as a precursor to spermidine and spermine and additionally has been shown to have a marked regulatory effect upon the polyamine biosynthetic pathway in that it has been shown that increased synthesis of putrescine is the first indication that a tissue will undergo renewed growth processes. Cadaverine which is the decarboxylation product of lysine has been shown to stimulate the activity of S-adenosyl-methionine decarboxylase and is known to be essential to growth processes of many microorganisms, for example, *H. parainfluenza*.

The compounds of general Formula I are irreversible inhibitors of ornithine decarboxylase and lysine decarboxylase rendering said compounds useful as antiinfective agents being effective in the control of microorganisms, for example, bacteria, fungi and viruses which are dependent upon polyamines for growth, for example, *E. coli*, Enterobacter, Klebsiella, *Staphylococcus aureus, C. cadaveris*, viruses such as, *H. parainfluenza*, picornaviruses, for example, encephalomyocarditis, *herpes simplex*, poxviruses and arboviruses, for example, *Semliki forest*. The compounds of general Formula I wherein A is methylene or ethylidene are also useful in the control of certain rapid growth processes. For example, said compounds are useful in the inhibition of spermatogenesis and embryogenesis and therefore the compounds find use as male antifertility agents and abortifacients. The compounds are also useful in the inhibition of the immune response, thus the compounds are useful as immunosuppressants for the treatment, for example, of myasthenia gravis, arthritis, multiple sclerosis and the prevention of tissue or organ transplant rejection, and are useful in the control of neoplastic growth, for example, solid tumors, leukemias and lymphomas. The compounds are also useful as inhibitors of prostatic hypertrophy, excessive scalp cell growth as found with the occurrence of dandruff and as inhibitors of abnormal cutaneous cell growth as found with a psoriatic condition. In administering the compounds of general Formula I wherein A is methylene or ethylene it may be desirable to administer concurrently by known procedures a monoamine oxidase inhibitor such as trans($\pm$)-2-phenylcycloproponamine or N-benzyl-N-methyl-2-propynylamine. The utility of compounds of general Formula I as irreversible inhibitors of ornithine or S-adenosylmethionine decarboxylase enzymes may be measured as follows. An aqueous solution of an appropriate compound is given orally or parenterally to male rats or mice. From 1 to 48 hours after administration of the compound the animals are sacrificed and the ventral lobes of the prostate removed and homogenized with the activity of ornithine and S-adenosylmethionine decarboxylases being measured as generally described strain measured by the general method described by Simler et al., Biochem. Pharmacol. 22, 1701 (1973) which is currently used to evidence antiepileptic activity.

The compounds of general Formula I wherein $R_2$ is hydrogen are useful as chemical intermediates for the preparation of novel cephalosporin derivatives of the following general Formula III, and the compounds of general Formula I wherein $R_2$ is COR and R is hydroxy are useful as chemical intermediates for the preparation of novel cephalosporin derivatives of the following general Formula IV. The cephalosporin compounds of Formulas III and IV are useful as antibiotics.

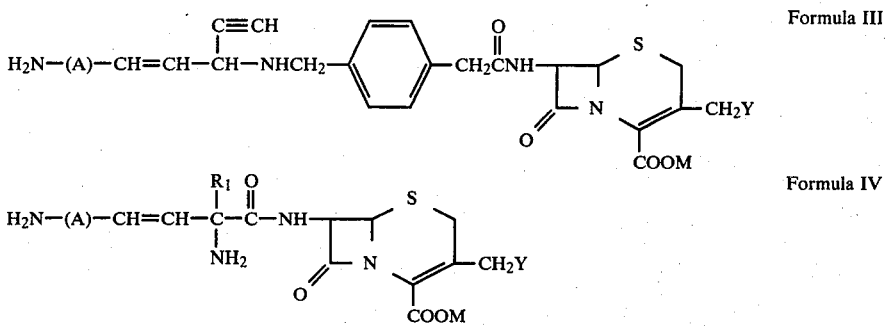

by E. A. Pegg and H. G. Willaims-Ashman, Biochem. J. 108, 533–539 (1968) and J. Janne and H. G. Williams-Ashman, Biochem. and Biophys. Res. Comm. 42, 222–228 (1971).

The compounds of general Formula I wherein A is methylene or ethylene are metabolic precursors of compounds having the following structure

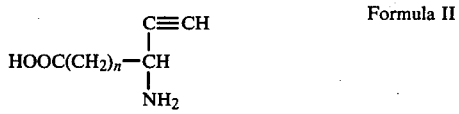

Formula II wherein n is 2 or 3 which are known to be irreversible inhibitors of γ-aminobutyric acid transaminase and upon administration results in higher brain levels of γ-aminobutyric acid (GABA). As precursors of γ-acetylenic-γ-aminobutyric acid the above-described compounds of Formula I are useful in the treatment of disorders of the central nervous system consisting of involuntary movement associated with Huntington's chorea, Parkinsonism, extra-pyramidal effects of drugs, for example, neuroleptics, seizure disorders associated with epilepsy, alcohol withdrawal, barbiturate withdrawal, psychoses associated with schizophrenia, depression, manic depression and hyperkinesis.

Several previous studies have shown that γ-aminobutyric acid is a major inhibitory transmitter of the central nervous system as reported, for example, by Y. Godin et al., Journal Neurochemistry, 16, 869 (1969) and that disturbance of the excitation and inhibition interplay can lead to diseases states such as Huntington's chorea (The Lancet, Nov. 9, 1974, pp. 1122–1123) Parkinsonism, schizophrenia, epilepsy, depression, hyperkinesis and manic depression disorders, Biochem. Pharmacol. 23, 2637–2649 (1974).

That the compounds of general Formula I wherein A is methylene or ethylene and $R_2$ is hydrogen are converted metabolically to the compounds of Formula II may be demonstrated by the protective effect of the compounds on audiogenic seizures in mice of the DBA In the above general Formulas III and IV A and $R_1$ have the meanings defined in general Formula I; M is hydrogen or a negative charge; and Y is hydrogen or acetoxy.

The compounds of general Formulas III and IV and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formulas III and IV and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formulas III and IV, salts and isomers thereof may be incorporated into creams or ointments.

Illustrative examples of bacteria against which the compounds of general Formulas III and IV and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes.*

Illustrative pharmaceutically acceptable non-toxic inorganic acid addition salts of the compounds of general Formula III are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of compounds of general Formulas III and IV are 7-[[2-[4-(1-acetylene-4-aminobut-2-enylaminomethyl)phenyl]acetyl]amino]-3-acetyloxymethyl-8-oxo-5-thia-1-azabicyclo[4.2.0]oct-2-ene-2-carboxylic acid and 7-[2-acetylene-2,5-diamino-1-oxopent-3-enamino]-3-acetyloxymethyl-8-oxo-5-thia-1-azabicyclo[4.2.0]oct-2-ene-2-carboxylic acid.

The preparation of the compounds of general Formulas III and IV is described hereinbelow.

As pharmacologically useful agents the compounds of general Formula I can be administered in various manners to the patient being treated to achieve the desired effect. The pharmacologically useful compounds of this invention can be used alone or in combination with one another. Also, the pharmacologically useful compounds of this invention may be administered in the form of a pharmaceutical preparation. The compounds may be administered orally, parenterally, for example, intravenously, intraperitoneally, or subcutaneously, or topically. The amount of compound administered will vary over a wide range and can be any effective amount. Depending on the patient to be treated, the condition being treated and the mode of administration, the effective amount of compound administered will vary from about 0.1 mg/kg to 500 mg/kg of body weight of the patient per unit dose and preferably will be about 10 mg/kg to about 100 mg/kg of body weight of patient per unit dose. For example, a typical unit dosage form may be a tablet containing from 10 to 300 mg of a compound of Formula I which may be administered to the patient being treated 1 to 4 times daily to achieve the desired effect.

As used herein the term patient is taken to mean warm blooded animals such as mammals, for example, cats, dogs, rats, mice, guinea pigs, horses, bovine cows, sheep and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment; the novel compounds are tableted with conventional tablet bases such as lactose, sucrose or corn starch in combination with binders such as acacia, corn starch or gelatin, disintegrating agents such as corn starch, potato starch, or alginic acid and a lubricant such as stearic acid, or magnesium stearate.

For parenteral administration the compounds may be adminstered injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general, water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

The compounds of general Formula I wherein each of $R_2$, $R_a$ and $R_b$ is hydrogen and A is methylene or ethylidene are prepared by treating 1 equivalent of a suitably protected propargylamine with a strong base, optionally in the presence of a divalent metal cation, for example, zinc iodide or magnesium bromide to form a protected propargylamine carbanion intermediate which is alkylated with 2-propenal or butenal then acylated with an acid halide, such as, alkanoyl halides, for example, acetyl chloride or propionyl chloride or aroyl halides, such as, benzoyl chloride or a lower alkyl haloformate, or tert-butoxycarbonylazide and subsequently hydrolyzed to an amide or carbamate of 1-amino-1-trimethylsilylacetylenebut-3-en-2-ol which is treated with a base, such as, sodium or potassium bicarbonate, sodium or potassium carbonate, sodium hydroxide or potassium hydroxide to give the carboxamide of 4-aminohex-1-en-5-yn-3-ol which is treated with trichloroacetonitrile in a solvent, such as, ethers, for example, diethyl ether, tetrahydrofuran, dioxane, dimethoxyethane, hydrocarbons, such as, benzene or toluene in the presence of a catalytic amount of a base such as sodium hydride, potassium tert-butoxide, lithium alkylamides, for example, lithium diisopropylamide or alkyl lithium at about −30° C. to 0° C. for about ½ hour to 3 hours to give the trichloromethylimidate ester which is heated to about 110° to 140° C. in a non-polar solvent, for example, xylene, toluene, nitrobenzene or chlorobenzene for about 1 to 10 hours to give the trichloromethyl acetamide which is hydrolyzed using aqueous acid, for example, hydrochloric acid or aqueous base, for example, sodium or potassium hydroxide.

The above described alkylation and acylation reaction may be carried out in an aprotic solvent, for example, benzene, toluene, ethers, tetrahydrofuran, dimethylsulfoxide or hexamethyl phosphortriamide. The reaction temperature varies from about −125° to 25° C. for about ½ hour to 24 hours.

Hydrolysis to give the amide of 1-amino-1-trimethylsilylacetylenebut-3-en-2-ol is achieved by treatment with hydrazine, phenylhydrazine or hydroxylamine or by treatment with mineral acids, for example, hydrochloric acid followed by treatment with an organic base such as triethylamine or pyridine in a lower alcoholic solvent, such as, methanol or ethanol at about 80° to 110° C. for about ½ hour to 2 hours.

The suitably protected propargylamine employed in the above reaction may be represented by the following general Formula V

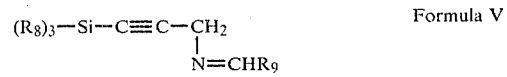

Formula V wherein $R_8$ is a straight or branched lower alkyl group having from 1 to 4 carbon atoms, such as, methyl, ethyl, n-propyl and tert-butyl or triethylmethyl. The compounds of Formula V are prepared by the addition of protecting groups on the acetylene function and the nitrogen function of propargylamine. Protection of the nitrogen function of the propargylamine is accomplished by forming in a known manner a Schiff's base with a non-enolizable carbonyl bearing compound selected from benzaldehyde, 2,2-dimethylpropanal and 2,2-diethylbutanal. Protection of the acetylenic function is accomplished by reacting the above-described Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

Suitable strong bases which may be employed in the above reaction to form the carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

The compounds of general Formula I wherein each of $R_2$, $R_a$ and $R_b$ is hydrogen and A is ethylene are prepared by treating 1-hydroxypent-2-enal with a metal acetylide of the formula HC≡CM' wherein M' is sodium, lithium or MgX' wherein X' is chlorine or bromine or with a complex of lithium acetylide/ethylenediamine in a solvent such as liquid ammonia, dimethylsulfoxide, ethers, for example, tetrahydrofuran, dioxane, diethyl ether or dimethoxyethane at about −30° to 25° C. for about 1 minute to 3 hours to give hept-3-en-5-yne-1,5-diol. When sodium or lithium acetylide are employed liquid ammonia is the preferred solvent. When lithium acetylide is employed ether solvents are also preferred. Ether solvents are preferred when magnesium halide is employed with preferred reaction temperatures of about 0° to 25° C. When the complex lithium acetylide-ethylenediamine is employed the preferred solvent is dimethylsulfoxide with a temperature of 25° C. and time of about 1 to 12 hours.

The diol derivative is treated with phthalimide, triphenylphosphine and diethyl diazodicarboxylate in ethers such as tetrahydrofuran, diethyl ether or dioxane for about 1 to 12 hours at about 25° to 50° C. to afford the corresponding diphthalimido derivative which is treated with hydrazine hydrate in a lower alcohol solvent such as methanol or ethanol for about 1 to 6 hours at about 25° to 50° C. followed by treatment with acid, for example, 6NHCl, for 1 to 10 hours at 100° C.

The compounds of general Formula I wherein $R_1$ is —C≡CH, each of $R_a$ and $R_b$ is hydrogen, A is methylene or ethylene, and $R_2$ is COR wherein R is hydroxy are prepared by treating the corresponding derivative wherein $R_2$ is hydrogen and wherein the amino groups and the acetylene group are suitably protected, having the structure

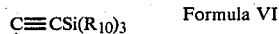
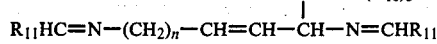

Formula VI with a strong base and acylating the thus formed carbanion intermediate followed by acid or base hydrolysis.

In the above general Formula VI $R_{10}$ is a straight or branched alkyl group having from 1 to 4 carbon atoms such as methyl, ethyl, n-propyl, isopropyl or n-butyl; $R_{11}$ is phenyl, tert-butyl or triethylmethyl; and n is the integer 1 or 2.

Suitable strong bases which may be employed in the above reaction to form each carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

Suitable acylating agents which may be employed in the above reaction are halo-formates, such as chloro methylformate or chloro ethylformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example, ethanol or isopropyl alcohol is required prior to deprotection by hydrolysis.

The acylating reaction may be carried out in an aprotic solvent, for example, benzene, toluene, ethers, tetrahydrofuran, dimethylsulfoxide, hexamethyl phosphortriamide. The reaction temperature varies from −120° C. to about 25° C., a preferred temperature being about −70° C., and the reaction time varies from about ½ hour to 24 hours.

Hydrolysis is achieved by treatment with aqueous acid, for example, hydrochloric acid, or aqueous base, for example, sodium hydroxide or potassium hydroxide.

The compounds of Formula VI are prepared by the addition of protecting groups on the acetylene function and the amino groups of a compound of the formula:

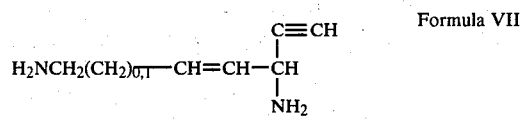

Formula VII

Protection of the amino groups is accomplished by forming in a known manner a Schiff's base with a non-enolizable carbonyl bearing compound selected from benzaldehyde, 2,2-dimethylpropanal and 2,2-diethylbutanal. Protection of the acetylenic function is accomplished by reacting the above-described Schiff's base with a trialkylsilyl chloride wherein the alkyl moiety has from 1 to 4 carbon atoms and is straight or branched, for example, trimethylsilylchloride or triethylsilylchloride forming in a known manner the corresponding trialkylsilyl derivative.

The compounds of general Formula I wherein $R_1$ is —CH═CH$_2$, $R_2$ is COR wherein R is hydroxy and each of $R_a$ and $R_b$ is hydrogen are prepared by treating the corresponding derivative wherein $R_1$ is —C≡CH with sodium, potassium or lithium in liquid ammonia and ammonium sulfate at about −70° to 25° C. until the blue color persists for about 15 minutes. These compounds may also be prepared by catalytic or organic semi-hydrogenation of the corresponding derivative wherein $R_1$ is —C≡CH, $R_2$ is COR and R is alkoxy and each of $R_a$ and $R_b$ is alkylcarbonyl. After reduction the protecting groups are removed by acid or base hydrolysis. Catalytic hydrogenation may be carried out in the presence of a base, for example, pyridine or triethylamine using inorganic catalysts as described by E. N. Marvell and I. Li, Synthesis, No. 8, August, 1973, pp. 457–468, for example, palladium-on-barium sulfate or the Lindlar catalyst, that is, lead-poisoned palladium-on-calcium carbonate. The hydrogenation process is continued until there is a reduction in the uptake of hydrogen.

The organic semi-hydrogenation is achieved by reacting equimolar amounts of the appropriate acetylene derivative and catecholborane under a nitrogen atmosphere at about 70° C. for about 2 hours by the general procedures described by H. C. Brown and S. K. Gupta, J. Am. Chem. Soc. 94, 4370–4371 (1972) and H. C. Brown, et al., J. Am. Chem. Soc. 95, 5786–5788 and 6456–6457 (1973).

The compounds of general Formula I wherein $R_8$ is

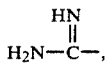

$R_2$ is hydrogen or COR wherein R is hydroxy and $R_b$ has the meaning defined in general Formula I are prepared by treating a compound of the formula

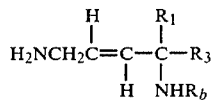

Formula VIII wherein $R_1$ and $R_b$ have the meanings defined in Formula I and $R_3$ is hydrogen or COOalkyl wherein the alkyl group has from 1 to 8 carbon atoms and is straight or branched, for example, methyl, ethyl, isopropyl or n-butyl, with the proviso that any free amino group is suitably protected with, for example, benzyloxycarbonyl, with an alkylisothiouronium salt, for example, ethylisothiouronium hydrobromide, by procedures generally known in the art; for example, *Organic Synthesis*, III, p. 440 (1955). The reaction is carried out in the presence of a base, such as, aqueous sodium hydroxide or potassium hydroxide at a pH of about 10 at a temperature of about 25° C. for about 6 to 60 hours after which the reaction mixture is neutralized with concentrated hydrochloric acid and the product isolated. When appropriate, protecting groups are removed by acid hydrolysis, for example, treatment with HBr in dioxane. The preparation of compounds of Formula VIII is described hereinbelow.

Following is described the preparation of compounds of general Formula I wherein $R_a$ and/or $R_b$ are other than hydrogen and $R_a$ is other than

including compounds of general Formula VIII. The following description is applicable to all the above said compounds, however, it is necessary to protect one or the other of the amino groups prior to treatment with the appropriate reactant, that is, acid halide or anhydride, alkyl haloformate or acid of the formula

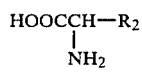

or anhydride thereof as described below to give compounds wherein either or both of $R_a$ and $R_b$ is other than hydrogen as follows: When $R_a$ is hydrogen and $R_b$ is other than hydrogen, the amino group to which $R_a$ is attached is protected as a phthalimido derivative by treating the corresponding derivative wherein $R_a$ is hydrogen and $R_2$ is hydrogen or COR wherein R is a straight or branched alkoxy group having from 1 to 8 carbon atoms, with a carbalkoxyphthalimide wherein the alkoxy moiety has from 1 to 4 carbon atoms, for example, carbethoxyphthalimide in a solvent such as an ether or a lower alcohol, such as, methanol, for ½ to 3 hours at about 0° to 50° C. followed by extraction with acid, for example, hydrochloric acid prior to treatment with the appropriate reactant described below to give compounds wherein $R_b$ is other than hydrogen. The phthalimide group is subsequently removed by treatment with hydrazine in a lower alcohol solvent, such as, methanol at about 50° to 100° C. for about 1 to 4 hours. The thus obtained compounds, that is, compounds wherein $R_a$ is hydrogen and $R_b$ is other than hydrogen may be treated with the appropriate reactants described below to give compounds wherein $R_a$ and $R_b$ are both other than hydrogen and $R_a$ is not

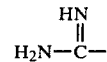

and may be the same or different. In preparing compounds wherein $R_a$ is other than hydrogen and $R_b$ is hydrogen the amino group to which $R_b$ is attached is protected with, for example, a benzyloxycarbonyl group by treatment of the corresponding derivative wherein $R_b$ is hydrogen and $R_2$ is hydrogen or COR wherein R is a straight or branched alkoxy group having from 1 to 8 carbon atoms with a benzyl haloformate, such as, benzyl chloroformate prior to treatment with the appropriate reactant described below to give compounds wherein $R_a$ is other than hydrogen or

The benzyloxy group is subsequently removed by acid hydrolysis, for example, by treatment with HBr in dioxane. When desired, the compounds thus obtained wherein $R_2$ is COR and R is a straight or branched alkoxy group having from 1 to 8 carbon atoms are hydrolyzed with base using for example, sodium hydroxide or sodium borate in an aqueous lower alcohol, for example, methanol, solvent for 2 to 4 hours at about 25° C. to give the corresponding acids, that is, compounds wherein R is hydroxy.

The compounds of general Formulas I and VIII wherein $R_a$ or $R_b$ is alkylcarbonyl wherein the alkyl moiety is straight or branched and has from 1 to 4 carbon atoms and $R_2$ is hydrogen or COR wherein R is hydroxy or a straight or branched alkoxy group having from 1 to 8 carbon atoms are prepared by treating the corresponding derivatives wherein $R_a$ or $R_b$ is hydrogen or is suitably protected or as to compounds of Formula I, $R_b$ is other than hydrogen as described above with an acid halide of the formula

wherein halo is a halogen atom, for example, chlorine or bromine and $R_{13}$ is a straight or branched alkyl group having from 1 to 4 carbon atoms or an appropriate acid anhydride, in water in the presence of a base such as sodium hydroxide or sodium borate at a temperature of about 0° to 25° C. for about ½ hour to 6 hours. When appropriate, protecting groups are removed as described hereinabove by treatment with hydrazine or acid.

The compounds of general Formula I and VIII wherein $R_a$ or $R_b$ is alkoxycarbonyl wherein the alkoxy moiety is straight or branched and has from 1 to 4 carbon atoms and $R_2$ is hydrogen or COR wherein R is hydroxy or a straight or branched alkoxy group having from 1 to 8 carbon atoms are prepared by treating the corresponding derivative wherein $R_a$ or $R_b$ is hydrogen or is suitably protected or as to compounds of Formula I, $R_b$ is other than hydrogen as described hereinabove with an alkyl haloformate of the formula

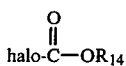

wherein halo is a halogen atom such as chlorine or bromine and $R_{14}$ is a straight or branched alkyl group having from 1 to 4 carbon atoms in water in the presence of a base such as sodium hydroxide or sodium borate at a temperature of about 0° to 25° C. for about ½ hour to 6 hours. When appropriate, protecting groups are removed as described hereinabove by treatment with hydrazine or acid.

The compounds of general Formulas I and VIII wherein $R_a$ or $R_b$ is

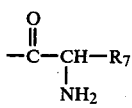

wherein $R_7$ is hydrogen, a straight or branched lower alkyl group of from 1 to 4 carbon atoms, benzyl or p-hydroxybenzyl and $R_2$ is hydrogen or COR wherein R is hydroxy or a straight or branched alkoxy group having from 1 to 8 carbon atoms are prepared by treating the corresponding derivative wherein $R_a$ or $R_b$ is hydrogen or is suitably protected or as to compounds of Formula I, $R_b$ is other than hydrogen as described hereinabove with an acid of the formula

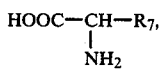

or an anhydride thereof, wherein the amino group is protected with a suitable blocking group such as benzyloxycarbonyl or tert-butoxycarbonyl and $R_7$ has the meaning defined hereinabove in an ether, such as, tetrahydrofuran or dioxane, methylene chloride or chloroform and in the presence of a dehydrating agent, such as, dicyclohexylcarbodiimide when the free acid is employed, at a temperature of about 0° to 35° C. for about 1 to 12 hours followed by acid and base hydrolysis and when appropriate, treatment with hydrazine to remove the protecting groups.

The compounds of the general Formula I wherein R is a straight or branched alkoxy group of from 1 to 8 carbon atoms may also be prepared by converting the corresponding compound wherein $R_1$ is hydroxy to the acid halide by, for example, treatment with thionyl chloride, followed by alcoholysis with an alcohol of the formula $R_8OH$ as defined above by procedures generally known in the art.

The compounds of this invention wherein R is $-NR_4R_5$ wherein each of $R_4$ and $R_5$ is hydrogen or a lower alkyl group of from 1 to 4 carbon atoms are prepared by an acylation reaction of an acid halide, for example, an acid chloride, of the corresponding compound wherein R is hydroxy and $R_a$ and $R_b$ have the meanings defined in general Formula I with the proviso that any free amino group is suitably protected with groups, such as, carbobenzyloxy or tert-butoxycarbonyl with an excess of an appropriate amine which may be represented as $HNR_4R_5$. The reaction is carried out in methylene chloride, chloroform, dimethyl formamide, or ethers such as tetrahydrofuran and dioxane, or benzene at about 25° C. for about 1 to 4 hours. Suitable amines are ammonia, or a compound which is a potential source of ammonia, for example, hexamethylenetetramine; primary amines, for example, methylamine, ethylamine or n-propylamine; and secondary amines, for example, dimethylamine, diethylamine, or di-n-butylamine. Following the acylation reaction the protecting groups are removed by treatment with acid, for example, trifluoroacetic acid or hydrogen bromide in dioxane.

The compounds of general Formula I wherein R is

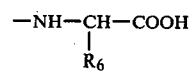

are prepared by reacting the corresponding derivative wherein R is hydroxy or a functional derivative thereof, such as, an acid anhydride and $R_a$ and $R_b$ have the meanings defined in Formula I with the proviso that any free amino group is protected with a suitable blocking group, such as, benzyloxycarbonyl, tert-butoxycarbonyl by reacting the amine protected free acid with a compound of the structure

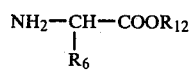

wherein $R_6$ has the meaning defined in general Formula I and $R_{12}$ is a lower alkyl group, for example, methyl or ethyl in an ether solution, such as, tetrahydrofuran or dioxane at about 0° C. to 35° C. for about 1 to 20 hours followed by acid then base hydrolysis, for example, with 2 N aqueous $NH_3$ at about 0° to 50° C. for about 1 to 20 hours, to remove the protecting group(s), with the proviso that when the amine protected free acid is employed the reaction is carried out using a dehydrating agent such as dicyclohexylcarbodiimide.

The individual optical isomers of the compounds of general Formula I wherein $R_a$ and $R_b$ are hydrogen and $R_2$ is hydrogen or COR wherein R is hydroxy may be separated by protecting the amino group distal to the acetylene function using carboethoxyphthalimide in a solvent such as tetrahydrofuran, diethyl ether or lower alcohols such as methanol or ethanol. When $R_2$ is COR and R is hydroxy the compound is first converted to the lower alkyl ester, for exaple, the methyl ester. The protected amine derivative is then resolved using either a (+) or (−) binaphthylphosphoric acid salt by the method described by R. Viterbo et al., in Tetrahedron Letters 48, 4617–4620 (1971) and in U.S. Pat. No. 3,848,030 or by using (+) camphor-10-sulfonic acid. The resolved phthalimido compound is then deprotected using hydrazine to remove the phthalimide group followed by acid or base hydrolysis to cleave the ester when $R_2$ is COR and R is hydroxy. The thus resolved acids and amines may be employed to prepare the individual isomers of compounds of the invention wherein $R_a$ or $R_b$ is other than hydrogen and $R_2$ is COR and R is other than hydroxy in the same manner as described hereinabove for the racemic mixtures of compounds wherein $R_a$ or $R_b$ is hydrogen and $R_2$ is hydrogen or COR wherein R is hydroxy.

The compounds of general Formula I wherein A is methylene, $R_1$ is —C≡CH, $R_2$ is COR wherein R is hydroxy and each of $R_a$ and $R_b$ is hydrogen, that is, 2-acetylene-2,5-diaminopent-3-enoic acid may also be prepared by treating a suitably protected propargylamine of Formula V with a strong base, alkylating the thus formed carbanion intermediate with alkylbromide, treating the alkylated intermediate with a strong base and acetylating the thus formed second carbanion intermediate with a suitable acylating reagent and subsequently removing the protecting groups by treatment with phenylhydrazine or hydrazine and a base such as potassium or sodium hydroxide to give 2-acetylene-2-aminopent-4-enoic acid. The acid is converted to the ester using methanol/HCl then treated with an acid halide such as a lower alkanoyl halide, for example, acetyl chloride or an aroyl halide, such as, benzoyl chloride or with a lower alkyl haloformate such as methyl chloroformate followed by treatment with an organic base such as pyridine or triethylamine and treating the thus formed ester amide in aqueous lower alcohols, such as, methanol or ethanol with selenium dioxide for 1 to 6 hours at about 80° to 110° C. to give the ester amide of 2-acetylene-2-amino-3-hydroxypent-4-enoic acid which is treated with trichloroacetronitrile in a solvent, such as, ethers, for example, diethyl ether, tetrahydrofuran, dioxane, dimethoxyethane, hydrocarbons, such as, benzene or toluene in the presence of a catalytic amount of a base such as sodium hydride, potassium tert-butoxide, lithium alkylamides, for example, lithium diisopropylamide or alkyl lithium at about −30° to 0° C. for about ½ hour to 3 hours followed by heating to about 110° to 140° C. in a non-polar solvent, for example, xylene, toluene, nitrobenzene, or chlorobenzene for about 1 to 10 hours and subsequently hydrolyzing with aqueous acid, for example, hydrochloric acid or aqueous base, for example, sodium hydroxide.

Suitable strong bases which may be employed in the above reaction to form each carbanion are those which will abstract a proton from the carbon atom adjacent to the acetylene moiety, such as, alkyl lithium, for example, butyl lithium or phenyl lithium, lithium di-alkylamide, for example, lithium diisopropylamide, lithium amide, tertiary potassium butylate or sodium amide.

Suitable acylating reagents which may be employed in the above reaction are halo-formates, such as chloro methylformate or chloro ethylformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example ethanol or isopropyl alcohol is required prior to deprotection by hydrolysis.

The acylating reaction may be carried out in an aprotic solvent, for example, benzene, toluene, ethers, tetrahydrofuran, dimethylsulfoxide, hexamethyl phosphortriamide. The reaction temperature varies from −120° C. to about 25° C., a preferred temperature being about −70° C., and the reaction time varies from about ½ hour to 24 hours.

EXAMPLE 1

7-[[2-[4-(1-Acetylene-5-aminopent-2-enylaminomethyl)phenyl]acetyl]amino]-3-acetyloxymethyl-8-oxo-5-thio-1-azabicyclo[4.2.0]oct-2-ene-2-carboxylic acid A mixture of 1 g of 3-acetyloxymethyl-7-[[2-[4-chloromethyl)phenyl]acetyl]amino]-8-oxo-5-thia-1-azabicyclo[4.2.0]oct-2-ene-2-carboxylic acid and 1 g of 1,5-hept-3-en-6-ynediamine wherein the amino group distal to the acetylene function is protected as phthalimido in 50 ml of ethanol was stirred at 25° C. for 24 hours after which the solvent is removed leaving a residue which is treated with hydrazine and chromatographed on silica gel using benzene-acetone as the eluant to give 7-[[2-[4-1-acetylene-5-aminopent-2-enylacetyl]amino]-3-acetyloxymethyl-8-oxo-5-thia-1-azabicyclo[4.2.0]oct-2-ene-2-carboxylic acid.

EXAMPLE 2

7-[2-Acetylene-2,5-diamino-1-oxopent-3-enamino]-3-acetyloxymethyl-8-oxo-5-thio-1-azabicyclo[4.2.0]oct-2ene-2-carboxylic acid A mixture of 1 g of 3-acetyloxymethyl-7-amino-8-oxo-5-thia-1-azabicyclo[4.2.0]oct-2-ene-2-carboxylic acid and 1 g of 2-acetylene-2,5-diaminopent-3-enoic acid chloride wherein the free amino groups are protected with tert-butoxycarbonyl in 50 ml of ethyl acetate is refluxed for 2 hours after which the solvent is removed leaving a residue which is chromatographed on silica gel using benzene-acetone as the eluant to give 7-[2-acetylene-2,5-diamino-1-oxopent-3-enamino]-3-acetoxymethyl-8-oxo-5-thia-1-azabicyclo[4.2.0]-oct-2-ene-2-carboxylic acid wherein the amino groups are protected with tert-butoxycarbonyl. The protected cephalosporin compound is treated with trifluoroacetic acid for ½ hour at 25° C. under nitrogen atmosphere then diluted with ether until precipitation stops and filtered to give the di-trifluoroacetic salt of the title cephalosporin which can be converted to the free base by use of ion exchange resin.

The following examples are illustrative of pharmaceutical preparations of compounds of general Formula I.

EXAMPLE 3

An illustrative composition for hard gelatin capsules is as follows:

| (a) | 1,4-hex-2-en-5-ynediamine | 20 mg |
|---|---|---|
| (b) | talc | 5 mg |
| (c) | lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3A

An illustrative composition for tablets is as follows:

| (a) | 2-acetylene-2,5-diaminopent-3-enoic acid | 20 mg |
|---|---|---|
| (b) | starch | 43 mg |
| (c) | lactose | 45 mg |

-continued

| | | |
|---|---|---|
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | | Weight percent |
|---|---|---|
| (a) | 2,5-hept-3-en-6-ynediamine | 1.0 |
| (b) | polyvinylpyrrolidone | 0.5 |
| (c) | lecithin | 0.25 |
| (d) | water for injection to make | 100.0 |

The materials (a)–(d) are mixed, homogenized and filled into 1 ml ampuls which are sealed and autoclaved 20 minutes at 121° C. Each ampul contains 10 mg per ml of novel compound (a).

The following examples further illustrate the compounds of the invention.

EXAMPLE 5

1,4-Hex-2-en-5-ynediamine dihydrochloride

A solution of 21.5 g (0.1 M) of 3-trimethylsilylprop-2-ynyl-1-iminobenzyl in 500 ml of tetrahydrofuran at −70° C. is treated with 66.5 ml of a 1.5 M solution of n-butyllithium. After 5 minutes at −70° C. a solution of zinc iodide, prepared from 8.0 g of zinc and 25.4 g of iodine in 100 ml of tetrahydrofuran, is added. The resulting solution is stirred at −70° C. for 20 minutes after which 5.6 g (0.1 M, 6.65 ml) of 2-propenal is added dropwise at −70° C. The solution is maintained at −70° C. for 30 minutes then 7.8 g (0.1 M, 7.0 ml) of acetyl chloride is added. The solution is allowed to warm to room temperature and diluted with ether, washed well with aqueous sodium bicarbonate followed by aqueous sodium chloride then dried over magnesium sulfate and evaporated leaving an oil which is taken up in 200 ml of isopropyl alcohol and treated with 10 g (0.093 M) of phenylhydrazene. The mixture is heated at reflux for 20 minutes then the solvent evaporated. The residue is dissolved in chloroform and applied to a column of silicon dioxide packed with chloroform. Elution with chloroform followed by 5% methanol/chloroform gives the acetamide of 1-trimethylsilylacetylene-1-aminobut-3-en-2-ol which is dissolved in 30 ml of methanol and treated with 2.5 g of potassium hydroxide in 30 ml of water at room temperature after which the methanol is filtered off.

The aqueous residue is saturated with sodium chloride and extracted well with methylene chloride. The organic phase is dried over magnesium sulfate and concentrated leaving a residue which is recrystallized from chloroform/petroleum ether to give the acetamide of 4-aminohex-1-en-5-yn-3-ol (M.P. 94° C.) of which 994 mg (6.5 mM) is taken up in 15 ml of tetrahydrofuran and added to 24 mg of a 50% dispension (0.5 mM) of sodium hydride. After 5 minutes at about 25° C. the solution is added dropwise via syringe to a solution of 935 mg (6.5 mM) of trichloroacetonitrile in 30 ml of tetrahydrofuran precooled to −23° C. (dry ice/carbon tetrachloride). The resulting solution is stirred for 1½ hours at −23° C. then evaporated at about 25° C. leaving an oil which is dissolved in 30 ml of xylene and heated at reflux for 3 hours then allowed to stand overnight at about 25° C. The resulting precipitate is collected, recrystallized from chloroform and combined with 40 ml of 6 N HCl and 100 ml of methanol. The solution is heated at reflux for 12 hours then concentrated. The resulting residue is washed well with chloroform, treated with charcoal, filtered and evaporated leaving a residue which is recrystallized from ethanol to give 1,4-hex-2-en-5-ynediamine dihydrochloride, M.P. 175° C. (dec.).

EXAMPLE 6

1,5-Hept-3-en-6-ynediamine

To a solution of sodium acetylide, prepared from 2.3 g (0.1 M) of sodium in 500 ml of ammonia, is added 35 g (35 mM) of 5-hydroxypent-2-enal. One hour later ammonium chloride is added and the ammonia allowed to evaporate. The residue is taken up in ether, filtered and concentrated leaving a residue which is taken up in 200 ml of tetrahydrofuran and stirred for 48 hours at 25° C. with 18.3 g (70 mM) of triphenylphosphine, 12.1 g (70 mM) of diethyl azodicarboxylate and 10.2 (70 mM) of phthalimide. The precipitate which forms is filtered off, recrystallized from methanol then dissolved in 30 ml of ethanol. The ethanol solution is treated with hydrazine hydrate (1.74 g) at reflux overnight after which the solvent is evaporated and the residue treated with 5% aqueous potassium hydroxide until basic, extracted with dichloromethane, evaporated and distilled to give 1.5-hept-3-en-6-ynediamine.

EXAMPLE 7

2-Acetylene-2,5-diaminopent-3-enoic acid hydrochloride

A solution of 2 g (18 mM) of 1,4-hex-2-en-5-ynediamine in 30 ml of benzene is treated with 3.8 g (36 mM) of benzaldehyde at 25° C. in the presence of magnesium sulfate. After 1 hour the solution is filtered and the benzene distilled off using a Dean-Stark apparatus leaving a residue which is distilled (Kugelrohr, 160° C., 0.1 mM) to give an oil which is taken up in 100 ml of tetrahydrofuran and treated with 14 ml of a 1.0 M solution (14 mM) of ethyl magnesium bromide at 0° C. After 30 minutes 1.5 g (14 mM) of chlorotrimethylsilane in 15 ml of tetrahydrofuran is added. The solution is stirred for 1 hour at 0° C. then brine is added and the mixture extracted with ether. The organic layer is washed well with brine, then dried and concentrated. The residue is distilled (Kugelrohr, 175° C., 0.1 mm) to afford an oil which is taken up in 10 ml of tetrahydrofuran and treated with lithium diisopropylamide, prepared from 8.4 mM of diisopropylamide and 4.2 ml of a 2 M solution of n-butyllithium, at −78° C. After 5 minutes 0.8 g (8.4 mM) of methyl chloroformate in 5 ml of tetrahydrofuran is added and the solution is immediately quenched with brine and extracted with ether. The ether extract is dried and evaporated leaving a residue which is refluxed in 50 ml of 6 N hydrochloric acid for three hours. On cooling the solution is extracted with methylenechloride. The aqueous solution is evaporated to dryness and the resulting residue triturated with ethanol. The insoluble salts are filtered off and the ethanol solution is treated with 800 mg (8.4 mM) of triethylamine. The resulting precipitate is filtered off and recrystallized from ethanol/water (9:1) to give 2-acetylene-2,5-diaminopent-3-enoic acid hydrochloride.

EXAMPLE 8

2,5-Diamino-2-vinylpent-3-enoic acid

To a suspension of 1.54 g (10 mM) of 2-acetylene-2,5-diaminopent-3-enoic acid and 2 g (1.4 mM) of ammonium sulfate in 100 ml of ammonia is added lithium at reflux until the blue color persists for 15 minutes after which ammonium chloride is added and the ammonia allowed to evaporate. The residue is dissolved in water and applied to a column of Amberlite 120 H+. The product is eluted with 2 M ammonium hydroxide and recrystallized from water/ethanol to give 2,5-diamino-2-vinylpent-3-enoic acid.

EXAMPLE 9

2-Acetylene-2,5-diaminopent-3-enoic acid

A solution of 21.5 g (0.1 M) of 3-trimethylsilylprop-2-ynyl-1-iminobenzyl in 600 ml of tetrahydrofuran at −78° C. is treated with 50 ml of a 2.0 M solution of n-butyllithium followed by the addition of 12.1 g (0.1 M) of allyl bromide After 3 hours at −78° C. 50 ml of a 2.0 M solution of n-butyllithium is added followed by the addition of 9.4 g (0.1 M) of methyl chloroformate. After 30 minutes at −78° C. the reaction mixture is treated with brine then extracted with ether. The ether solution is dried over magnesium sulfate and evaporated to afford an oil which is dissolved in 100 ml of pentane and treated with 10.8 g (0.1 M) of phenylhydrazine. After 1 hour at 25° C. the precipitate is filtered off and the filtrate evaporated and treated with 12 g (0.7 M) of potassium hydroxide in 40 ml of methanol and 40 ml of water overnight at 25° C. The methanol is evaporated off and the aqueous solution washed with dichloromethane, acidified using 6 N hydrochloric acid, rewashed with dichloromethane and evaporated to dryness. The residue is triturated with ethanol, filtered and the filtrate evaporated leaving a residue which is dissolved in water. The pH of the water solution is adjusted to 6 and applied to an Amberlite resin. Elution with 1 M ammonium hydroxide affords 2-acetylene-2-aminopent-4-enoic acid which is treated overnight at 25° C. with methanol saturated with dry HCl after which the solvent is evaporated to give the methyl ester hydrochloride. The methyl ester hydrochloride (10 g, 0.05 M) is suspended in 20 ml of dichloromethane and treated with 10 g (0.1 M) of triethylamine and 3.9 g (0.05 M) of acetyl chloride overnight at 25° C. The solution is then washed with water, dried and evaporated leaving a residue which is recrystallized from ethylacetate to give methyl 2-acetylene-2-(1-oxoethylamino)pent-4-enoate (10 mM) which is taken up in 20 ml of ethanol and 5 ml of water and treated with 1.11 g (10 mM) of selenium dioxide. The mixture is heated to reflux for 4 hours after which the solvent is evaporated. The resulting residue is taken up in ether and washed with sodium bicarbonate solution. The ether solution is dried, evaporated and the mixture of diastereomeric alcohols purified by chromatography of Florisil. The alcohol is dissolved in 15 ml of tetrahydrofuran and added to 24 mg of a 50% dispension (0.5 mM) of sodium hydride. After 5 minutes at about 25° C. the solution is added dropwise via syringe to a solution of 935 mg (6.5 mM) of trichloromethylacetonitrile in 15 ml of tetrahydrofuran precooled to −23° C. The resulting solution is stirred for 1½ hours at −23° C. then evaporated at about 25° C. leaving an oil which is dissolved in 30 ml of xylene and heated to reflux for 3 hours then allowed to stand overnight at about 25° C. The precipitate is collected, recrystallized from chloroform and combined with 40 ml of methanol and 40 ml of 6 N HCl and heated at reflux for 12 hours then concentrated. The resulting residue is washed well with chloroform, treated with charcoal, filtered and evaporated leaving a residue which is recrystallized from ethanol to give 2-acetylene-2,5-diaminopent-3-enoic acid.

When in the procedure of Example 5 an appropriate amount of 2-butenal is substituted for 2-propenal, 2,5-hept-3-en-6-ynediamine dihydrochloride is obtained.

When in the procedure of Example 7 an appropriate amount of 1,5-hept-3-en-6-ynediamine is substituted for 1,4-hex-2-en-5-ynediamine, 2-acetylene-2,6-diaminohex-3-enoic acid is obtained.

EXAMPLE 10

N-(1-Acetylene-4-aminobut-2-enyl)acetamide

A solution of 242 mg (1 mM) of N-(4-acetylene-4-aminobut-2-enyl)phthalimide in 10 ml of chloroform is treated with 1 ml of triethylamine followed by 78 mg (1 mM) of acetyl chloride in 5 ml of chloroform. After 1 hour at 25° C. the solution is washed with water, dried and concentrated. The resulting residue is dissolved in 10 ml of ethanol and treated with 60 mg (1.1 mM) of hydrazine hydrate at reflux for 2 hours after which the solvent is evaporated. The residue is treated with 1 N sodium hydroxide solution until the solid dissolves then is extracted with dichloromethane. The organic phase is dried and concentrated to give N-(1-acetylene-4-aminobut-2-enyl)acetamide.

N-(4-Acetylene-4-aminobut-2-enyl)phthalimide used in the above procedure is prepared as follows. A solution of 13.5 g (61.6 mM) of carbethoxyphthalimide in 70 ml of tetrahydrofuran is added dropwise to a solution of 6.91 g (61.6 mM) of 1-acetylene-1,4-but-2-endiamine in 30 ml of tetrahydrofuran in an ice-bath. After completion of the addition the mixture is stirred for 2 hours at 25° C. then diluted with ether, and the solution is extracted with 1 N hydrochloric acid (3×100 ml). The aqueous phase is washed several times with ether then concentrated to dryness leaving a residue which is recrystallized from ethanol to give N-(4-acetylene-4-aminobut-2-enyl)phthamlimide HCl which is converted to the free base.

When in the procedure of Example 10 an appropriate amount of ethyl chloroformate is used in place of acetyl chloride, N-(1-acetylene-4-aminobut-2-enyl)ethyl carbamate is obtained.

When in the procedure of Example 10 an appropriate amount of benzyl chloroformate is substituted for acetyl chloride, N-(1-acetylene-4-aminobut-2-enyl)benzyl carbamate is obtained.

EXAMPLE 11

N-(4-Acetylene-4-aminobut-2-enyl)-2-aminopropionamide

A solution of 492 mg (2 mM) of N-(1-acetylene-4-amino-but-2-enyl)benzyl carbamate in 4 ml of dichloromethane is treated with 446 mg (2 mM) of N-carbobenzoxyalanine and 412 mg (2 mM) of N,N'-dicyclohexylcarbodiimide for about 15 hours at 25° C. after which the solution is cooled to 0° C. and the precipitated dicyclohexylurea filtered off. The filtrate is diluted with 20 ml of dichloromethane and washed with 1 N hydrochloric acid, water and aqueous sodium bicarbonate, then dried and concentrated. The resulting residue is treated with 6 ml of a 40% (w/w) solution of hydrogen bromide in dioxane at 25° C. for 30 minutes then diluted with ether and the precipitated N-(4-acetylene-4-aminobut-2-enyl)-2-aminopropionamide dihydrobromide collected.

EXAMPLE 12

N-(4-Acetylene-4-aminobut-2-enyl)acetamide

A solution of 492 mg (2 mM) of N-(1-acetylene-4-aminobut-2-enyl)benzyl carbamate in 10 ml of chloroform is treated with 202 mg (2 mM) of triethylamine followed by 160 mg (2.1 mM) of acetyl chloride. After 1 hour at 25° C. the solution is washed with water, dilute hydrochloric acid, and aqueous sodium carbonate, then dried and concentrated. The resulting residue is treated with 6 ml of a 40% (w/w) solution of hydrogen bromide in dioxane for 30 minutes at 25° C., then ether is added on the precipitated N-(4-acetylene-4-aminobut-2-enyl)acetamide hydrobromide is collected.

When in the above procedure an appropriate amount of ethyl chloroformate is substituted for acetyl chloride, N-(4-acetylene-4-aminobut-2-enyl)ethyl carbamate is obtained.

EXAMPLE 13

N-(1-Acetylene-4-aminobut-2-enyl)-2-aminopropionamide di HBr

A solution of 450 mg (2 mM) of N-carbobenzoxyalanine in 10 ml of dichloromethane is treated with 202 mg (2 mM) of triethylamine followed by 218 mg (2 mM) of ethyl chloroformate. After 1 hour at 25° C. the solution is treated with 484 mg (2 mM) of N-(4-acetylene-4-aminobut-2-enyl)phthalimide in 10 ml of chloroform and maintained at 25° C. for one hour after which the solution is washed with 1 N hydrochloric acid, water and aqueous sodium carbonate then dried and concentrated. The residue is dissolved in 15 ml of ethanol and treated with 110 mg (2 mM) of hydrazine hydrate at reflux for 2 hours after which the solvent is evaporated. The residue is treated with 5% aqueous sodium hydroxide and extracted with dichloromethane. The organic phase is dried and concentrated and the resulting residue is treated with 5 ml of a 40% (w/w) solution of hydrogen bromide in dioxane. After 30 minutes at 25° C. the mixture is treated with ether and the precipitated N-(1-acetylene-4-aminobut-2-enyl)-2-aminopropionamide dihydrobromide collected.

EXAMPLE 14

1-Acetylene-1,4-but-2-enylene-bis-2-aminopropionamide di HBr

A solution of 900 mg (4 mM) of N-carbobenzoxyalanine in 10 ml of dichloromethane is treated with 405 mg (4 mM) of triethylamine followed by 435 mg (4 mM) of ethyl chloroformate. After 1 hour at 25° C. the solution is treated with 224 mg (2 mM) of 1-acetylene-1,4-but-2-enediamine in 5 ml of dichloromethane. The solution is maintained at 25° C. for 1 hour then is washed with water, dried and concentrated. The resulting residue is treated with 6 ml of a 40% (w/w) solution of hydrogen bromide in dioxane for 30 minutes at 25° C. then diluted with ether. The precipitate is collected to afford 1-acetylene-1,4-but-2-enylene-bis-2-aminopropionamide dihydrobromide.

EXAMPLE 15

1-Acetylene-1,4-but-2-enylene-bis-acetamide

A solution of 0.5 g (4.5 mM) of 1-acetylene-1,4-but-2-endiamine in 50 ml of ether containing 0.91 g (9.0 mM) of triethylamine is treated with 0.7 g (9.0 mM) of acetyl chloride. After 1 hour the ether solution is washed with brine, dried and evaporated to afford 1-acetylene-1,4-but-2-enylene-bis-acetamide.

EXAMPLE 16

Methyl 2-acetylene-2,5-diaminopent-3-enoate di HCl

2-Acetylene-2,5-diaminopent-3-enoic acid (500 mg, 3.2 mM) is added to 40 ml of methanol which had been saturated with dry hydrogen chloride. The solution is heated at reflux for 12 hours, then the solvent is evaporated to afford methyl 2-acetylene-2,5-diaminopent-3-enoate dihydrochloride.

EXAMPLE 17

2-Acetylene-2,5-di-(1-oxoethylamino)pent-3-enoic acid

To a solution of 312 mg (2.0 mM) of 2-acetylene-2,5-diaminopent-3-enoic acid in 2.5 ml of 1 N sodium hydroxide at 0° C. are added simultaneously from two syringes 312 mg (4 mM) of acetyl chloride diluted in 1 ml of THF and 4 ml of 1 N sodium hydroxide. After 30 minutes at 0° C. the solution is acidified by the addition of 6 N hydrochloric acid, then extracted well with dichloromethane. The organic phase is dried and concentrated to afford 2-acetylene-2,5-di-(1-oxoethylamino)pent-3-enoic acid.

In a similar manner only substituting an appropriate amount of ethyl chloroformate for acetyl chloride, 2-acetylene-2,5-di-(1-ethoxycarbonylamino)pent-3-enoic acid is obtained.

EXAMPLE 18

2-Acetylene-2,5-di-N-(2-aminopropylcarbonylamino)-pent-3-enoic acid

A solution of 240 mg (1 mM) of methyl 2-acetylene-2,5-diaminopent-3-enoate dihydrochloride in 4 ml of methylene chloride containing 200 mg of triethylamine is treated with 440 mg (2 mM) of N-carbobenzoxy alanine and 412 mg (2 mM) of N,N'-dicyclohexylcarbodiimide overnight at 25° C. The mixture is then cooled to 0° C. and the precipitated dicyclohexyl urea filtered off. The filtrate is diluted with methylene chloride, washed with water, bicarbonate, dilute hydrochloric acid, then dried and concentrated. The residue is treated with 10 ml of ethanol and 10 ml of a 40% (w/w) solution of hydrogen bromide in dioxane for 30 minutes at 25° C. after which 50 ml of ether is added and the resulting precipitate collected. The precipitate is treated with 15 ml of 1 N aqueous sodium hydroxide overnight at 25° C. The pH of the solution is adjusted to neutral and the product isolated from an Amberlite 120 H+ resin by elution with 2 M ammonium hydroxide to give 2-acetylene-2,5-di-N-(2-aminopropylcarbonylamino)pent-3-enoic acid.

EXAMPLE 19

N-Propyl-2-acetylene-2,5-diaminopent-3-enamide dihydrobromide

To a solution of 312 mg (2 mM) of 2-acetylene-2,5-diaminopent-3-enoic acid di HBr acid in 2.5 ml of 1 N aqueous sodium hydroxide at 0° C. are added simultaneously from two syringes 680 mg (4 mM) of benzyl chloroformate in dioxane (2 ml) and 4 ml of 1 N sodium hydroxide. After 30 minutes at 0° C. the solution is acidified by the addition of 6 N hydrochloric acid, then extracted well with dichloromethane. The organic phase is dried and concentrated to afford 2-acetylene-2,5-di-(benzyloxycarbonylamino)pent-3-enoic acid which is dissolved in 15 ml of dichloromethane and treated with 220 mg of thionyl chloride at 25° C. for one hour. Propylamine (250 mg) is then added and the solution stirred at 25° C. for one hour, then washed with water, dried and concentrated. The residue is treated with 12 ml of a solution of dioxane containing hydrogen bromide (40% w/w) and allowed to stand for 30 minutes at 25° C. Ether (50 ml) is then added and the resulting precipitate collected to afford N-propyl-2-acetylene-2,5-diaminopent-3-enamide dihydrobromide.

EXAMPLE 20

2-(2-Acetylene-2,5-diamino-1-oxopent-3-enylamino)-propionic acid

To 424 mg (1 mM) of 2-acetylene-2,5-di-(benzyloxycarbonylamino)pent-3-enoic acid in 15 ml of methylene chloride is added 205 mg (2 mM) of triethylamine followed 109 mg (1 mM) of ethyl chloroformate. The solution is stirred for one hour at 25° C., then 103 mg (1 mM) of alanine methyl ester in 5 ml of methylene chloride is added. This solution is kept overnight at 25° C., washed with water, dried and evaporated to dryness. The residue is treated with 10 ml of a 40% (w/w) solution of hydrogen bromide in dioxane at 25° C. for 30 minutes. Ether (50 ml) is then added and the precipitate collected. The precipitate is treated with 40 ml of a 1 N sodium hydroxide solution overnight at 25° C., the pH adjusted to 6.5, and applied to an Amberlite 120 H+ resin. Elution with 2 N ammonium hydroxide affords 2-(2-acetylene-2,5-diamino-1-oxopent-3-enylamino)propionic acid.

EXAMPLE 21

Methyl 2-acetylene-2,5-di-(1-oxoethylamino)pent-3-enoate

A solution of 170 mg (1 mM) of 2-acetylene-2,5-di(1-oxoethylamino)pent-3-enoic acid in 10 ml of chloroform is cooled to −5° C. and 78 mg of thionyl chloride in chloroform is added. After 30 minutes 1 ml of methanol is added. Evaporation of the solvent yields methyl 2-acetylene-2,5-di-(1-oxoethylamino)pent-3-enoate.

Alternatively the compounds of general Formula I wherein A is methylene, $R_1$ is —C≡CH, $R_2$ is COOH and each of $R_a$ and $R_b$ is hydrogen may also be prepared by treating 1 equivalent of a tert-butyl carbamate of 1-amino-1-trimethylsilylacetylenebut-3-en-2-ol with 1 equivalent of trichloroacetonitrile in a solvent, such as, ethers, for example, diethyl ether, tetrahydrofuran, dioxane, dimethoxyethane, hydrocarbons, such as, benzene or toluene in the presence of a catalytic amount of a base such as sodium hydride, potassium tert-butoxide, lithium alkylamides, for example, lithium diisopropylamide or alkyl lithium at 110° to 140° C. in a non-polar solvent, for example, xylene, toluene, nitrobenzene or chlorobenzene for about 1 to 10 hours to give the trichloromethyl acetamide which is treated with trifluoroacetic acid at about 0° to 25° C. for about ½ hour to 3 hours followed by treatment with 1 equivalent of benzaldehyde at about 0° to 25° C. for about 1 to 3 hours to give N-(4-benzylimino-4-trimethylsilylacetylenebut-2-enyl)trichloromethylacetamide which is treated with 2 equivalents of a strong base, such as, an alkyl lithium, for example, butyl lithium or phenyl lithium, lithium dialkylamide, such as, lithium diisopropylamide, lithium amide, tertiary potassium butylate or sodium amide followed by acylation with a suitable acylating reagent and subsequent hydrolysis using aqueous acid, for example, hydrochloric or toluene sulfonic acid.

Suitable acylating reagents for use in the above reaction are for example, halo-formates, such as, methyl chloroformate, azido tert-butylformate, cyanogen bromide, carbon dioxide, diethylcarbonate, phenylisocyanate, triethoxymethylium tetrafluoroborate, N,N-dimethylcarbamoyl chloride, 2-methylthio-1,3-dithiolinium iodide, ethylene carbonate or ethylene trithiocarbonate. When 2-methylthio-1,3-dithiolinium iodide is employed the additional step of alcoholysis with a lower alcohol, for example, ethanol or isopropyl alcohol is required prior to deprotection by hydrolysis. The acylating reaction is generally carried out at about −120° C. to 25° C., preferably −70° C. and for about ½ hour to 24 hours in an aprotic solvent, for example, benzene, toluene, ethers, such as, tetrahydrofuran, dimethylsulfoxide, or hexamethylphosphortriamide. The following specific example further illustrates the process.

EXAMPLE 22

2-Acetylene-2,5-diaminopent-3-enoic acid

A solution of 21.5 g (0.1 M) of 3-trimethylsilylprop-2-ynyl-1-iminobenzyl in 500 ml of tetrahydrofuran at −70° C. is treated with n-butyllithium (66.7 ml of a 1.5 M solution) and five minutes later a solution of zinc iodide, prepared from 8.0 g of zinc and 25.4 g (0.1 M) of iodide in 100 ml of tetrahydrofuran, is added. The resulting solution is stirred at −70° C. for 20 minutes after which 5.6 g (0.1 M, 6.65 ml) of 2-propenal is added dropwise at −70° C. The solution is maintained at −70° C. for 30 minutes then 14.7 g (0.1 M) of tert-butoxycarbonyl azide is added. The solution is allowed to warm to room temperature, diluted with ether, washed well with aqueous sodium bicarbonate, followed by aqueous sodium chloride, dried over magnesium sulfate and evaporated to afford an oil which is taken up in 200 ml of isopropyl alcohol, treated with 10 g (0.093 M) of phenylhydrazine, heated to reflux for 20 minutes then evaporated. The resulting residue is dissolved in chloroform and applied to a column of silicon dioxide (300 g) packed with chloroform. Elution with chloroform followed by 5% methanol/chloroform gives the carbamate of 1-amino-1-trimethylsilylacetylenebut-3-en-2-ol, 1.94 g (6.5 mM) of which is dissolved in 15 ml of tetrahydrofuran and added to sodium hydride (24 mg of a 50% dispension, 0.5 mM). After 5 minutes at room temperature this solution is added dropwise via syringe to a solution of 935 mg (6.5 mM) of trichloroacetonitrile in 30 ml of tetrahydrofuran precooled to −23° C. The resulting solution is stirred for 1-½ hours at −23° C. then evaporated at room temperature leaving an oil which is dissolved in xylene and heated to reflux for 3 hours then allowed to stand overnight at room temperature. The resulting precipitate is collected and recrystallized from chloroform to give a white solid 4.0 g (10 mM) of which is added to 4 ml of trifluoroacetic acid at 0° C. Thirty minutes later the solvent is evaporated leaving a residue which is suspended in 20 ml of dichloromethane and 1.0 g (10 mM) of benzaldehyde and 2 g of triethylamine are added. The mixture is stirred for 4 hours at 25° C. then washed well with water, dried and evaporated. The resulting residue is recrystallized from ethyl acetate, and 4.1 g (10 mM) of the solid in 10 ml of tetrahydrofuran is added to lithium diisopropylamide, prepared from 2.02 g (20 mM) of diisopropylamine and 10 ml of a 2 M solution (20 mM) of n-butyllithium, containing 10 ml of hexamethylphosphortriamide at −78° C. After 20 minutes at −78° C., 940 mg (10 mM) of methyl chloroformate in 5 ml of tetrahydrofuran is added and after 30 minutes at −78° C. 600 mg of acetic acid is added followed by water. The mixture is extracted with ether, the ether solution washed with brine, dried and concentrated. The resulting residue is treated with 30 ml of 6 N HCl and 30 ml of ethanol for 24 hours at reflux. On cooling the solution is washed with dichloromethane then concentrated to dryness leaving a residue which is taken up in the minimum quantity of water. The pH of the aqueous solution is adjusted to 6 and applied to an Amberlite resin 120 H+. Elution with 1 M ammonium hydroxide affords 2-acetylene-2,5-diaminopent-3-enoic acid which is recrystallized from water/ethanol.

EXAMPLE 23

2-Acetylene-2-amino-5-guanidinopent-3-enoic acid

To a solution of 1.9 g (10 mM) of 2-acetylene-2,5-diaminopent-3-enoic acid monohydrochloride in 10 ml of 2 M sodium hydroxide solution is added 3.7 g (20 mM) of ethylthiouronium hydrobromide. The pH of the solution is maintained at 10 by the addition of 2 M sodium hydroxide during 48 hours at 28° C. after which the pH is adjusted to 6, and the solution applied to an Amberlite resin 120 H+. The product is eluted with 2 M ammonium hydroxide solution and recrystallized from methanol-water to give 2-acetylene-2-amino-5-guanidinopent-3-enoic acid.

EXAMPLE 24

2-Acetylene-2-acetamido-5-aminopent-3-enoic acid (A) A solution of 1.68 g (10 mM) of methyl 2-acetylene-2,5-diaminopent-3-enoate in 15 ml of tetrahydrofuran is added to 2.2 g (10 mM) of N-carboethoxyphthalimide in 30 ml of tetrahydrofuran at 0° C. After 3 hours at 25° C. the solution is diluted with ether then extracted with 1 N HCl. The aqueous phase is washed with ether then concentrated to dryness leaving a residue which is recrystallized from ethanol to give methyl 2-acetylene-2-amino-5-phthalimidopent-3-enoate hydrochloride.

(B) A solution of 3.0 g (10 mM) of methyl 2-acetylene-2-amino-5-phthalimidopent-3-enoate, prepared from the hydrochloride obtained above, in 50 ml of chloroform is treated with 2.0 g (20 mM) of triethylamine followed by treatment with 780 mg (10 mM) of acetyl chloride. After 1 hour at 25° C. the solution is washed with 1 N HCl, dried and concentrated to give methyl 2-acetylene-2-acetamido-5-phthalimidopent-3-enoate which is dissolved in 100 ml of ethanol. The ethanol solution is treated with 600 mg (10 mM) of hydrazine hydrate at reflux for 2 hours then the solvent is evaporated. The remaining residue is treated with 1 N sodium hydroxide until the solid dissolves then extracted with dichloromethane. The organic phase is dried and concentrated to give methyl 2-acetylene-2-acetamido-5-aminopent-3-enoate which is treated with 40 ml of 2 N sodium hydroxide at 25° C. for 4 hours after which the pH is adjusted to 6, and the solution is applied to an Amberlite 120 H+ resins. Elution with 2 M sodium hydroxide gives 2-acetylene-2-acetamido-5-aminopent-3-enoic acid.

When in procedure (B) above an appropriate amount of benzyl chloroformate or ethyl chloroformate is substituted for acetyl chloride, 2-acetylene-2-benzyloxycarbonylamino-5-aminopent-3-enoic acid and 2-acetylene-2-ethoxycarbonylamino-5-aminopent-3-enoic acid are obtained respectively.

EXAMPLE 25

2-Acetylene-2-amino-5-acetamidopent-3-enoic acid

A solution of 2.8 g (10 mM) of methyl 2-acetylene-2-benzyloxycarbonylamino-5-aminopent-3-enoate prepared by treating 2-acetylene-2-benzyloxycarbonylamino-5-aminopent-3-enoic acid with methanol saturated with HCl, in 20 ml of chloroform is treated with 1 g (10 mM) of triethylamine followed by treatment with 780 mg (10 mM) of acetyl chloride. After 1 hour at 25° C. the solution is washed with 1 N HCl, dried and evaporated. The resulting residue is treated with 30 ml of a 40% (w/w) solution of hydrogen bromide in dioxane for 30 minutes at 25° C. then ether is added and the precipitated 2-acetylene-2-amino-5-acetamidopent-3-enoic acid hydrobromide collected.

EXAMPLE 26

N-Propyl 2-acetylene-2-acetamido-5-aminopent-3-enamide

Methyl 2-acetylene-2-acetamido-5-phthalimidopent-3-enoate (3.4 g, 10 mM) is treated with 40 ml of 2 N sodium hydroxide at 25° C. for 4 hours after which the solution is acidified and extracted well with dichloromethane. The organic phase is dried and concentrated to afford 2-acetylene-2-acetamido-5-phthalimidopent-3-enoic acid. The acid is dissolved in 40 ml of chloroform and treated with 1.2 g (10 mM) of thionyl chloride at 25° C. for 4 hours after which 1.2 g (20 mM) of propylamine is added. The solution is stirred at 25° C. for 2 hours then washed with 1 N HCl, dried and concentrated to afford N-propyl-2-acetylene-2-acetamido-5-phthalimidopent-3-enamide. The amide is dissolved in 40 ml of ethanol and treated with 600 mg (10 mM) of hydrazine hydrate at reflux for 2 hours. The solution is then concentrated, and the residue treated with 1 N sodium hydroxide until the solid dissolves then extracted well with dichloromethane. The organic phase is dried and concentrated to afford N-propyl-2-acetylene-2-acetamido-5-aminopent-3-enamide.

EXAMPLE 27

2-Acetylene-2-(2-aminopropionamido)-5-aminopent-3-enoic acid

A solution of 2.1 g (10 mM) of N-carbobenzoxyalanine in 50 ml of dichloromethane is treated with 1.0 g (10 mM) of triethylamine followed by 1.1 g (10 mM) of ethyl chloroformate. After 1 hour at 25° C. the solution is treated with 3.0 g (10 mM) of methyl 2-acetylene-2-amino-5-phthalimidopent-3-enoate in 40 ml of chloroform and maintained at 25° C. for 1 hour after which the solution is washed with 1 N HCl, water and aqueous sodium carbonate then dried and concentrated. The residue is dissolved in 60 ml of ethanol and treated with 550 mg (10 mM) of hydrazine hydrate at reflux for 2 hours, after which the solvent is evaporated. The residue is treated with 5% aqueous sodium hydroxide and extracted with dichloromethane. The organic phase is dried and concentrated, and the resulting residue is treated with 5 ml of a 40% (w/w) solution of hydrogen bromide in dioxane. After 30 minutes at 25° C. the mixture is treated with ether and the precipitated methyl 2-acetylene-2-(2-aminopropionamido)-5-aminopent-3-enoate dihydrobromide collected. The ester dihydrobromide salt is treated with 40 ml of 2 N sodium hydroxide for 4 hours at 25° C., the pH is adjusted to 6 and the solution is applied to an Amberlite 120 H+ resin. Elution with 2 M ammonium hydroxide affords 2-acetylene-2-(2-aminopropionamide)-5-aminopent-3-enoic acid.

EXAMPLE 28

Methyl 2-acetylene-2-amino-5-(2-aminopropionamido)pent-2-enoate dihydrobromide and 2-acetylene-2-amino-5-(2-aminopropionamido)pent-2-enoic acid A solution of 2.9 g (10 mM) of methyl 2-acetylene-2-benzyloxycarbonylamino-5-aminopent-3-enoate in 40 ml of dichloromethane is treated with 2.20 mg (10 mM) of N-carbobenzoxyalanine and 2.1 g (10 mM) of N,N'-dicyclohexylcarbodiimide for about 15 hours at 25° C. after which the solution is cooled to 0° C. and the precipitated dicyclohexylurea filtered off. The filtrate is diluted with 20 ml of dichloromethane and washed with 1 N hydrochloride acid, water and aqueous sodium bicarbonate, then dried and concentrated. The resulting residue is treated with 40 ml of a 40% (w/w) solution of hydrogen bromide in dioxane at 25° C. for 30 minutes then diluted with ether. The precipitate is collected to afford methyl 2-acetylene-2-amino-5-(2-aminopropionamido)pent-2-enoate dihydrobromide. The methyl ester dihydrobromide is treated with 40 ml of 2 N sodium hydroxide for 4 hours at 25° C. The pH of the solution is adjusted to 6 and applied to an Amberlite resin 120 H+. Elution with 2 M ammonium hydroxide affords 2-acetylene-2-amino-5-(2-aminopropionamido)-pent-2-enoic acid.

When R is a straight or branched alkoxy group of from 1 to 8 carbon atoms, reacting an acid halide of the corresponding derivative wherein R is hydroxy with an alcohol of the formula $R_8$-OH wherein $R_8$ is a straight or branched alkyl group having from 1 to 8 carbon atoms, saturated with HCl gas at about 25° C. for from 12 to 36 hours.

We claim:
1. A compound of the formula

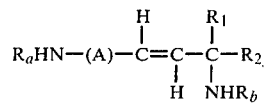

wherein A is methylene, ethylene or ethylidene; $R_1$ is —C≡CH; $R_2$ is hydrogen; $R_a$ is hydrogen,

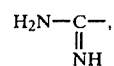

alkylcarbonyl wherein the alkyl moiety has from 1 to 4 carbon atoms and is straight or branched, alkoxycarbonyl wherein the alkoxy moiety has from 1 to 4 carbon atoms and is straight or branched, or

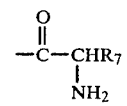

wherein $R_7$ is hydrogen, a straight or branched lower alkyl group of from 1 to 4 carbon atoms, benzyl, or p-hydroxybenzyl; $R_b$ has the same meaning as defined for $R_a$ except $R_b$ is not

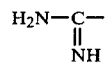

and $R_a$ and $R_b$ can be the same or different; with the proviso that when $R_a$ is

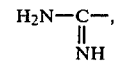

A is methylene; and pharmaceutically acceptable salts and individual isomers thereof.

2. A compound of claim 1 wherein $R_a$ and/or $R_b$ is hydrogen.

3. A compound of claim 1 which is 1,4-hex-2-en-5-ynediamine or a pharmaceutically acceptable salt thereof.

4. A compound of claim 1 which is 2,5-hept-3-en-6-ynediamine or a pharmaceutically acceptable salt thereof.

* * * * *